Nov. 2, 1965 E. S. BOERNER Plant Pat. 2,569
ROSE PLANT
Filed Aug. 21, 1964
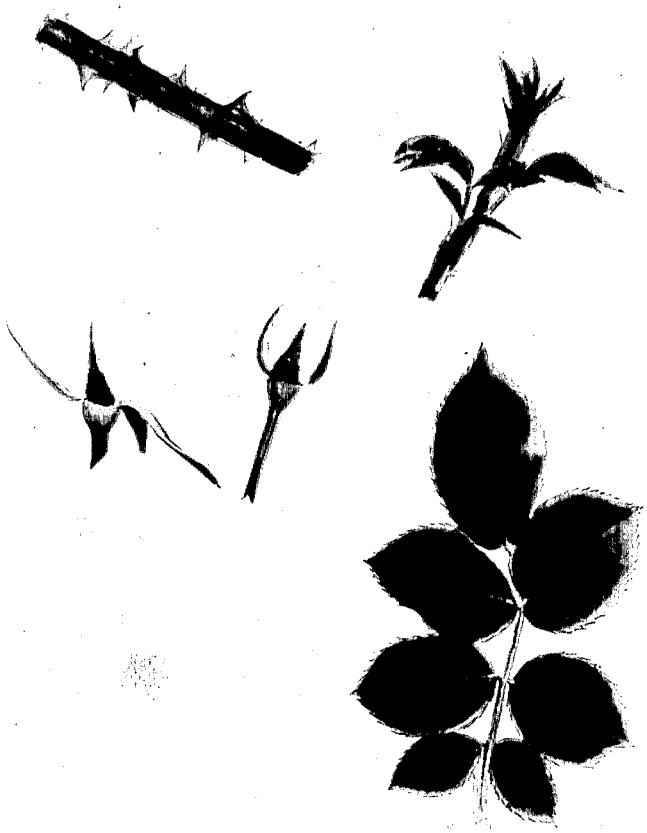
Inventor.
E. S. Boerner
By: Robb & Robb
Attorneys.

United States Patent Office

Plant Pat. 2,569
Patented Nov. 2, 1965

2,569
ROSE PLANT

Eugene S. Boerner, Newark, N.Y., assignor to Jackson & Perkins Company, Newark, N.Y., a corporation of New York

Filed Aug. 21, 1964, Ser. No. 391,348
1 Claim. (Cl. Plt.—20)

The present invention relates to a new and distinct variety of rose plant of the hybrid tea class, which was originated by me by crossing an unnamed and unpatented hybrid tea seedling of "Garnette" (unpatented) with the variety "Hawaii" (Plant Patent No. 1,833).

The primary objective of this breeding was to produce a new rose variety of the hybrid tea class, which achieves greater flower production, with the flower having stiffer petals than the parent variety "Hawaii." This objective was fully achieved, along with other desirable improvements, as evidenced by the following unique combination of characteristics which are outstanding in the new variety and which distinguish it from its parents, as well as from all other vareties of which I am aware:

(1) A vigorous habit of plant growth;

(2) Greater flower petalage than the flowers of the parent variety "Hawaii";

(3) A firm upright position of the flower petals;

(4) Good resistance of the flower petals to wind and rain; and (5) A distinctive and attractive general color tonality of the flowers corresponding to Scarlet Red, lightly overcast with Scarlet.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgeway's Color Standards and Nomenclature:

Parentage: Seedling.
- *Seed parent.*—An unnamed seedling of "Garnette."
- *Pollen parent.*—"Hawaii."

Classification:
- *Botanic.*—Hybrid tea.
- *Commercial.*—Hybrid tea.

*Flower*

(Observations made from specimens grown outdoors at Newark, New York, in the early morning during the latter part of the month of June.)

Blooming habit: Recurrent—continuous.

Bud:
- *Size.*—Large.
- *Form.*—Ovoid; is not affected by wet or hot weather.
- *Color.*—When sepals first divide—Nopal Red, Plate 1. When petals begin to unfurl—Spectrum Red, Plate 1. When half-blown—Scarlet Red, Plate 1, very lightly overcast with Rose Doree, Plate 1 on the edge of the petal, on the inside; reverse of petals—Spectrum Red, Plate 1, lightly overcast with Scarlet Red, Plate 1 and with the lower half of the petal lightened with Begonia Rose, Plate 1.
- *Sepals.*—Slightly branched; curl back when petals begin to unfurl. Color: inside—Olivine, Plate 32; outside—Cress Green, Plate 31.
- *Calyx.*—Color—Biscay Green, Plate 17. Shape—apple. Size—small. Aspect—smooth. Odor when rubbed—none.
- *Peduncle.* — Length — long. Aspect — smooth. Strength—erect; heavy. Color—Light Elm Green, Plate 17.
- *Opening.*—Opens up well; is not affected by adverse weather conditions.

Bloom:
- *Size.*—Large. Average size when fully expanded—4½ inches.
- *Borne.*—Both singly and several together.
- *Stems.*—Long; strong.
- *Form (when first open).*—Full open. Permanence—retains its form to the end.
- *Petalage.*—Double (full but open center); firm petals; very resistant to wind and rain.
- *Number of petals under normal conditions.*—From 35 to 40.
- *Color.*—Center of flower—Scarlet Red, Plate 1, overcast with Scarlet, Plate 1. Outer petals—Spectrum Red, Plate 1, lightly overcast with Scarlet Red, Plate 1. Base of petals (aiglet)—Clear Dull Green-Yellow, Plate 17. Inside of petals—Scarlet Red, Plate 1, lightly overcast with Scarlet, Plate 1. Reverse of petals—Scarlet Red, Plate 1, very lightly overcast with Rose Doree, Plate 1. General tonality from a distance—Scarlet Red, Plate 1, lightly overcast with Scarlet, Plate 1.
- *Discoloration.*—General tonality at end of first day—Scarlet Red, Plate 1, overcast with Scarlet, Plate 1. Second day—Scarlet Red, Plate 1, lightly overcast with Scarlet, Plate 1. Third day—Scarlet Red, Plate 1, lightly overcast with Scarlet, Plate 1.

Petals:
- *Texture.*—Thick and firm; is not affected by wet or hot weather.
- *Appearance.*—Inside—satiny. Outside—shiny.
- *Form.*—Oval.
- *Arrangement.*—Imbricated (regularly arranged shingle-like).
- *Petaloids in center.*—Few; large.
- *Persistence.*—Drop off cleanly.
- *Fragrance.*—Moderate. Nature—tea (average hybrid tea scent).
- *Lasting quality.*—On the plant—long. As cut flower—long.

*Genital organs*

Stamens, anthers: Medium size; many; regularly arranged around styles. Color—Yellow-Ocher, Plate 15.

Stamens, filaments (threads): Medium length. Color—Pale-Ochraceous Buff, Plate 15.

Pollen: Color—Sea-Foam Yellow, Plate 31.

Styles: Columnar; uneven length; short; thin.

Stigmas: Color—Light Buff, Plate 15.

Ovaries: All enclosed in calyx.

Hips: None.

Seeds: None.

*Plant*

Form: Bush.

Growth: Vigorous; upright.

Foliage: Compound of 5 to 7 leaflets.
- *Size.*—Large.
- *Quantity.*—Normal.
- *Color.*—New foliage: upper side—Courge Green, Plate 17, lightly overcast with Carmine, Plate 1; under side—Oxblood Red, Plate 1. Old foliage: upper side—Varley's Green, Plate 18; under side—Jade Green, Plate 18.
- *Shape.*—Oval pointed.
- *Texture.* — Upper side — leathery. Under side—smooth.

*Ribs and veins.*—Ordinary.
*Edge.*—Serrated (saw toothed).
*Serration.*—Both double and single; sharp.
*Leaf stem.*—Color—Deep Grape Green, Plate 41. Under side—smooth.
*Stipules.*—Medium length; bearded.

Wood:

*New wood.*—Color—Light Bice Green, Plate 17. Bark—smooth.
*Old wood.*—Color—Spinach Green, Plate 5. Bark—smooth.

Thorns:

*Thorns.*—Quantity: on main stalks from base—many; on laterals from stalk—ordinary. Form—flat base; medium length; some hooked downward and some hooked upward. Color (when young)—Mignonette Green, Plate 31. Position—irregular.
*Prickles.*—Quantity: on main stalks—none; on laterals—none.

*Short needles.*—Quantity: on main stalks—none; on laterals—none.

I claim:

A new and distinct variety of rose plane of the hybrid tea class, substantially as herein shown and described, characterized particularly as to novelty by the unique combination of a vigorous habit of plant growth, greater flower petalage than the flowers of the parent variety "Hawaii," a firm upright position of the flower petals, good resistance of the flower petals to wind and rain, and a distinctive and attractive general color tonality of the flowers corresponding to Scarlet Red, lightly overcast with Scarlet.

No references cited.

ABRAHAM G. STONE, *Primary Examiner.*